(12) United States Patent
Bremer et al.

(10) Patent No.: US 6,620,468 B2
(45) Date of Patent: Sep. 16, 2003

(54) DIOXANE DERIVATIVES, AND LIQUID-CRYSTALLINE MEDIUM

(75) Inventors: Matthias Bremer, Darmstadt (DE); Peer Kirsch, Darmstadt (DE); Detlef Pauluth, Ober-Ramstadt (DE); Sabine Schoen, Darmstadt (DE); Kazuaki Tarumi, Seeheim (DE); Georg Lüssem, Ober-Ramstadt (DE); Michael Heckmeier, Ober-Ramstadt (DE); Joachim Krause, Dieburg (DE)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 115 days.

(21) Appl. No.: 09/921,892

(22) Filed: Aug. 6, 2001

(65) Prior Publication Data

US 2002/0130300 A1 Sep. 19, 2002

(30) Foreign Application Priority Data

Aug. 11, 2000 (DE) .......................... 100 39 378

(51) Int. Cl.$^7$ ................. C09K 19/34; C09K 19/30; C07D 319/06; C07D 407/02
(52) U.S. Cl. ............. 428/1.1; 252/299.61; 252/299.63; 549/369; 549/370
(58) Field of Search .............. 549/369, 370; 252/299.61, 299.63, 299.66; 428/1.1; 570/131, 132, 127

(56) References Cited

U.S. PATENT DOCUMENTS 5,348,677 A * 9/1994 Poetsch et al. .......... 252/299.6

FOREIGN PATENT DOCUMENTS

| DE | 19748109 | * 5/1999 |
| DE | 19807371 | * 8/1999 |
| DE | 19807372 | * 8/1999 |
| DE | 19945890 | * 4/2000 |
| DE | 10058472 | * 6/2001 |

* cited by examiner

Primary Examiner—Shean C. Wu
(74) Attorney, Agent, or Firm—Millen, White, Zelano & Branigan, P.C.

(57) ABSTRACT

The invention relates to novel dioxane derivatives of the formula I

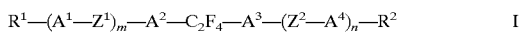

in which $R^1$, $R^2$, $A^1$, $A^2$, $A^3$, $A^4$, $Z^1$, $Z^2$, m and n are as defined herein, to their use as components of liquid-crystalline media, and to liquid-crystal and electro-optical display elements which contain the liquid-crystalline media according to the invention.

19 Claims, No Drawings

DIOXANE DERIVATIVES, AND LIQUID-CRYSTALLINE MEDIUM

The invention relates to tetrafluoroethylene-bridged dioxane derivatives, to their use as components of liquid-crystalline media, and to liquid-crystal and electro-optical display elements which contain the liquid-crystalline media according to the invention.

The dioxane derivatives according to the invention can be used as components of liquid-crystalline media, in particular for displays based on the principle of the twisted cell, the guest-host effect, the effect of deformation of aligned phases DAP or ECB (electrically controlled birefringence), the IPS (in-plane switching) effect or the effect of dynamic scattering.

The substances employed hitherto for this purpose all have certain disadvantages, for example inadequate stability to the action of heat, light or electric fields, or unfavorable elastic and/or dielectric properties.

The invention has an object of finding novel stable liquid-crystalline or mesogenic compounds which are suitable as components of liquid-crystalline media, in particular for TN, STN, IPS and TFT displays.

Upon further study of the specification and appended claims, further objects and advantages of this invention will become apparent to those skilled in the art.

It has now been found that tetrafluoroethylene-bridged dioxane derivatives according to the invention are eminently suitable as components of liquid-crystalline media. With their aid, stable liquid-crystalline media, particularly suitable for TFT or STN displays, can be obtained. The novel compounds are distinguished, in particular, by high thermal stability, which is advantageous for a high holding ratio, and exhibit favorable clearing point values.

Through a suitable choice of the ring members and/or the terminal substituents, the physical properties of the dioxane derivatives according to the invention can vary within broad ranges. Thus, it is possible, for example, to obtain dioxane derivatives according to the invention which have very small optical anisotropy values or have low positive to highly positive dielectric anisotropy values.

In particular, the dioxane derivatives according to the invention are distinguished by high clearing points at the same time as unexpectedly low rotational viscosity. Preferably, the clearing points are $\geq 65°$ C.

Liquid-crystalline media having very low optical anisotropy values are particularly suitable for reflective and transflective applications, i.e. applications in which the respective LCD experiences no or only supporting background illumination. Further, it is preferred that the media exhibit a mesophase range of at least 80° C., more preferably at least 90° C. and most preferably at least 100° C. Furthermore, preferred values for the optical anisotropy of the medium are $\leq 0.08$, more preferably $\leq 0.07$ and particularly $\leq 0.06$.

The provision of the dioxane derivatives according to the invention very generally considerably broadens the range of liquid-crystalline substances which are suitable, from various applicational points of view, for the preparation of liquid-crystalline mixtures.

The dioxane derivatives according to the invention have a broad range of applications. Depending on the choice of substituents, these compounds can serve as base materials of which liquid-crystalline media are predominantly composed; however, it is also possible to add liquid-crystalline base materials from other classes of compound to the dioxane derivatives according to the invention in order, for example, to modify the dielectric and/or optical anisotropy of a dielectric of this type and/or to optimize its threshold voltage and/or its viscosity.

In the pure state, the dioxane derivatives according to the invention are colourless and form liquid-crystalline mesophases in a temperature range which is favorably located for electro-optical use. They are stable chemically, thermally and to light.

The invention thus relates to tetrafluoroethylene-bridged dioxane derivatives of the formula I

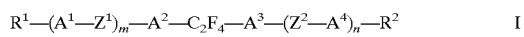

in which $R^1$ and $R^2$, independently of one another, are H, —CN, —F, Cl, —OCN, —NCS, —NO$_2$, or an alkyl radical having 1–12 carbon atoms which is unsubstituted or monosubstituted or polysubstituted by halogen, CN or CF$_3$, and in which one or more CH$_2$ groups may each, independently of one another, be replaced by —O—, —S—, —CO—, —CO—O—, —O—CO—, —O—CO—O—, —CH=CH—, —CH=CF—, —CF=CF—, —C≡C— or

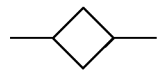

in such a way that S and/or O atoms are not linked directly to one another, $A^1$, $A^2$, $A^3$ and $A^4$, independently of one another, are a) trans-1,4-cyclohexylene, in which, in addition, one or more non-adjacent CH$_2$ groups may be replaced by —O— and/or —S—, b) 1,4-phenylene, in which, in addition, one or two CH groups may be replaced by N, c) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or d) 1,4-cyclohexenylene, in which the radicals a), b) and d) may also be substituted by CN or halogen, and where at least one of the radicals $A^1$, $A^2$, $A^3$ and $A^4$ is 1,3-dioxane-2,5-diyl, $Z^1$ and $Z^2$ are each, independently of one another, —O—, —CH$_2$O—, —OCH$_2$—, —CO—O—, —O—CO—, —CF$_2$O—, —OCF$_2$—, —CF$_2$CF$_2$—, —CH$_2$CH$_2$—, —CH=CH—, —CH=CF—, —CF=CF—, —C≡C— or a single bond, and m and n, independently of one another, are 0, 1 or 2, where m+n is 0, 1 or 2.

The invention furthermore relates to the use of compounds of the formula I as components of liquid-crystalline media.

The invention furthermore relates to a liquid-crystalline medium having at least two liquid-crystalline components which comprises at least one compound of the formula I.

The invention furthermore relates to a liquid-crystal display element, in particular an electro-optical display element, which contains, as dielectric, a liquid-crystalline medium according to the invention.

Particular preference is given to reflective and transflective liquid-crystal display elements and other liquid-crystal displays having low birefringence Δn, so-called "low Δn mode displays", such as, for example, reflective TN displays. Preference is furthermore given to IPS ("in plane switching") mode liquid-crystal displays.

The meaning of the formula I covers all isotopes of the chemical elements bound in the compounds of the formula I. In enantiomerically pure or enriched form, the compounds of the formula I are also suitable as chiral dopants and in general for achieving chiral mesophases.

Above and below, n, m, $R^1$, $R^2$, $A^1$, $A^2$, $A^3$, $A^4$, $Z^1$ and $Z^2$ are as defined, unless expressly stated otherwise. If the radical $A^1$ occurs more than once, it may adopt identical or different meanings. The same applies to all other groups which occur more than once.

Particular preference is given to compounds of the formula I having two, three or four six-membered rings, in particular those which contain one or two 1,3-dioxane-2,5-diyl radicals.

Preference is furthermore given to compounds of the formula I which, besides the dioxane radicals, contain at least one, preferably one or more, trans-1,4-cyclohexylene radicals.

Preference is furthermore given to compounds of the formula I in which $R^1$ and $R^2$ are alkyl and alkoxy having 1 to 12 carbon atoms or alkenyl or alkenyloxy having 2 to 10 carbon atoms.

$A^1$, $A^2$, $A^3$ and $A^4$ are preferably 1,3-dioxane-2,5-diyl, trans-cyclohexane-1,4-diyl or unsubstituted or substituted 1,4-phenylene.

Preference is given to compounds of the formula I in which n is 1 or 2, and $A^4$ is 1,4-phenylene which is monosubstituted or disubstituted by F or CN, in particular

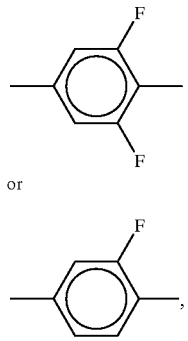

or and $R^2$ is F, Cl, CN or halogenated alkyl or alkoxy having 1 to 5 carbon atoms or halogenated alkenyl having 2 to 6 carbon atoms.

$Z^1$ and $Z^2$ are preferably —$CH_2CH_2$—, —CH=CH—, —C≡C—, —$CF_2CF_2$—, —CF=CF—, —$CF_2O$—, —$OCF_2$— or a single bond, in particular a single bond, —$CH_2$—$CH_2$— or —$CF_2CF_2$—.

Compounds of the formula I in which $R^1$ is straight-chain alkyl or alkoxy having 1 to 10 carbon atoms or alkenyl having 2 to 10 carbon atoms and $Z^1$ and/or $Z^2$ are —$CF_2CF_2$— or a single bond are particularly preferred.

Preferred compounds of the formula I are bicyclic compounds of the sub-formula Ia

   Ia tricyclic compounds of the sub-formula Ib

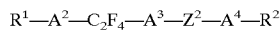   Ib and tetracyclic compounds of the sub-formulae Ic and Id

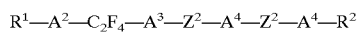   Ic

   Id

Particular preference is given to compounds of the sub-formulae Ia, Ib and Ic.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical, and Bco denotes a bicyclo[2.2.2]octylene radical, Dec denotes a decahydronaphthalene radical, where Cyc and/or Phe may be unsubstituted or monosubstituted or polysubstituted by $CH_3$, Cl, F or CN. Q is $C_2F_4$, Z has one of the meanings indicated for $Z^1$ in the formula I.

$R^1$ and $R^2$ are preferably alkyl or alkoxy having 1 to 12 carbon atoms or alkenyl or alkenyloxy having 2 to 10 carbon atoms.

$A^1$, $A^2$, $A^3$ and $A^4$ are preferably Phe, Cyc, Che, Pyd, Pyr or Dio, in particular Phe, Cyc or Dio. The compounds of the formula I preferably contain not more than one of the radicals Bco, Dec, Pyd, Pyr or Dit.

Phe is preferably

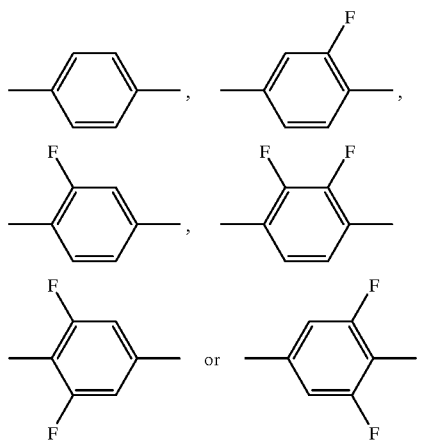

The terms 1,3-dioxane-2,5-diyl and Dio each cover the two positional isomers

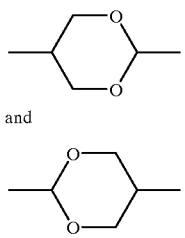

and

Halogen is preferably F or Cl, in particular F.

The cyclohexene-1,4-diyl group preferably has the following structures:

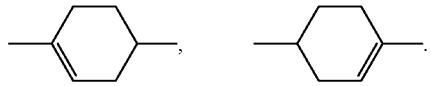

If the rings $A^1$ and $A^4$ (m or n=2) are present more than once, the two rings may have identical or different meanings. The same also applies to the bridges $Z^1$ and $Z^2$ and to all further groups which occur more than once in the compounds of the formula I.

Particularly preferred bicyclic compounds of the sub-formula Ia include the following sub-formulae:

| | |
|---|---|
| $R^1$-Dio-Q-Cyc-$R^2$ | Ia1 |
| $R^1$-Dio-Q-Phe-$R^2$ | Ia2 |
| $R^1$-Dio-Q-Dio-$R^2$ | Ia3 | where the compounds of sub-formulae Ia1 and Ia2 are very particularly preferred.

Particularly preferred tricyclic compounds of the sub-formula Ib include the following sub-formulae:

| | |
|---|---|
| $R^1$-Cyc-Q-Cyc-Z-Dio-$R^2$ | Ib1 |
| $R^1$-Cyc-Q-Dio-Z-Cyc-$R^2$ | Ib2 |
| $R^1$-Dio-Q-Cyc-Z-Cyc-$R^2$ | Ib3 |
| $R^1$-Dio-Q-Dio-Z-Cyc-$R^2$ | Ib4 |
| $R^1$-Dio-Q-Cyc-Z-Dio-$R^2$ | Ib5 |
| $R^1$-Cyc-Q-Dio-Z-Dio-$R^2$ | Ib6 |
| $R^1$-Dio-Q-Cyc-Z-Phe-$R^2$ | Ib7 |
| $R^1$-Dio-Q-Phe-Z-Cyc-$R^2$ | Ib8 |
| $R^1$-Cyc-Q-Dio-Z-Phe-$R^2$ | Ib9 |
| $R^1$-Cyc-Q-Phe-Z-Dio-$R^2$ | Ib10 |
| $R^1$-Phe-Q-Dio-Z-Cyc-$R^2$ | Ib11 |
| $R^1$-Phe-Q-Cyc-Z-Dio-$R^2$ | Ib12 |
| $R^1$-Dio-Q-Dio-Z-Phe-$R^2$ | Ib13 |
| $R^1$-Dio-Q-Phe-Z-Dio-$R^2$ | Ib14 |
| $R^1$-Phe-Q-Dio-Z-Dio-$R^2$ | Ib15 |
| $R^1$-Phe-Q-Phe-Z-Dio-$R^2$ | Ib16 |
| $R^1$-Phe-Q-Dio-Z-Phe-$R^2$ | Ib17 |
| $R^1$-Dio-Q-Phe-Z-Phe-$R^2$ | Ib18 | where the compounds of sub-formulae Ib1, Ib2, Ib3, Ib7 and Ib9 are very particularly preferred.

Particularly preferred tetracyclic compounds of the sub-formulae Ic and Id include the following sub-formulae:

| | |
|---|---|
| $R^1$-Cyc-Q-Cyc-Z-Dio-Z-Phe-$R^2$ | Ic1 |
| $R^1$-Cyc-Q-Cyc-Z-Phe-Z-Dio-$R^2$ | Ic2 |
| $R^1$-Cyc-Q-Cyc-Z-Dio-Z-Cyc-$R^2$ | Ic3 |
| $R^1$-Cyc-Q-Cyc-Z-Cyc-Z-Dio-$R^2$ | Ic4 |
| $R^1$-Cyc-Q-Cyc-Z-Dio-Z-Dio-$R^2$ | Ic5 |
| $R^1$-Cyc-Q-Dio-Z-Dio-Z-Phe-$R^2$ | Ic6 |
| $R^1$-Cyc-Q-Dio-Z-Phe-Z-Dio-$R^2$ | Ic7 |
| $R^1$-Cyc-Q-Dio-Z-Dio-Z-Cyc-$R^2$ | Ic8 |
| $R^1$-Cyc-Q-Dio-Z-Cyc-Z-Dio-$R^2$ | Ic9 |
| $R^1$-Cyc-Q-Dio-Z-Dio-Z-Dio-$R^2$ | Ic10 |
| $R^1$-Cyc-Q-Dio-Z-Phe-Z-Cyc-$R^2$ | Ic11 |
| $R^1$-Cyc-Q-Dio-Z-Cyc-Z-Phe-$R^2$ | Ic12 |
| $R^1$-Cyc-Q-Dio-Z-Cyc-Z-Cyc-$R^2$ | Ic13 |
| $R^1$-Cyc-Q-Dio-Z-Phe-Z-Phe-$R^2$ | Ic14 |
| $R^1$-Cyc-Q-Phe-Z-Dio-Z-Phe-$R^2$ | Ic15 |
| $R^1$-Cyc-Q-Phe-Z-Phe-Z-Dio-$R^2$ | Ic16 |
| $R^1$-Cyc-Q-Phe-Z-Dio-Z-Cyc-$R^2$ | Ic17 |
| $R^1$-Cyc-Q-Phe-Z-Cyc-Z-Dio-$R^2$ | Ic18 |
| $R^1$-Cyc-Q-Phe-Z-Dio-Z-Dio-$R^2$ | Ic19 |
| $R^1$-Dio-Q-Cyc-Z-Dio-Z-Phe-$R^2$ | Ic20 |
| $R^1$-Dio-Q-Cyc-Z-Phe-Z-Dio-$R^2$ | Ic21 |
| $R^1$-Dio-Q-Cyc-Z-Dio-Z-Cyc-$R^2$ | Ic22 |
| $R^1$-Dio-Q-Cyc-Z-Cyc-Z-Dio-$R^2$ | Ic23 |
| $R^1$-Dio-Q-Cyc-Z-Dio-Z-Dio-$R^2$ | Ic24 |
| $R^1$-Dio-Q-Cyc-Z-Phe-Z-Cyc-$R^2$ | Ic25 |
| $R^1$-Dio-Q-Cyc-Z-Cyc-Z-Phe-$R^2$ | Ic26 |
| $R^1$-Dio-Q-Cyc-Z-Cyc-Z-Cyc-$R^2$ | Ic27 |
| $R^1$-Dio-Q-Cyc-Z-Phe-Z-Phe-$R^2$ | Ic28 |
| $R^1$-Dio-Q-Dio-Z-Dio-Z-Phe-$R^2$ | Ic29 |
| $R^1$-Dio-Q-Dio-Z-Phe-Z-Dio-$R^2$ | Ic30 |
| $R^1$-Dio-Q-Dio-Z-Dio-Z-Cyc-$R^2$ | Ic31 |
| $R^1$-Dio-Q-Dio-Z-Cyc-Z-Dio-$R^2$ | Ic32 |
| $R^1$-Dio-Q-Dio-Z-Dio-Z-Dio-$R^2$ | Ic33 |
| $R^1$-Dio-Q-Dio-Z-Phe-Z-Cyc-$R^2$ | Ic34 |
| $R^1$-Dio-Q-Dio-Z-Cyc-Z-Phe-$R^2$ | Ic35 |
| $R^1$-Dio-Q-Dio-Z-Cyc-Z-Cyc-$R^2$ | Ic36 |
| $R^1$-Dio-Q-Dio-Z-Phe-Z-Phe-$R^2$ | Ic37 |
| $R^1$-Dio-Q-Phe-Z-Dio-Z-Phe-$R^2$ | Ic38 |
| $R^1$-Dio-Q-Phe-Z-Phe-Z-Dio-$R^2$ | Ic39 |
| $R^1$-Dio-Q-Phe-Z-Dio-Z-Cyc-$R^2$ | Ic40 |
| $R^1$-Dio-Q-Phe-Z-Cyc-Z-Dio-$R^2$ | Ic41 |
| $R^1$-Dio-Q-Phe-Z-Dio-Z-Dio-$R^2$ | Ic42 |
| $R^1$-Dio-Q-Phe-Z-Phe-Z-Cyc-$R^2$ | Ic43 |
| $R^1$-Dio-Q-Phe-Z-Cyc-Z-Phe-$R^2$ | Ic44 |
| $R^1$-Dio-Q-Phe-Z-Cyc-Z-Cyc-$R^2$ | Ic45 |
| $R^1$-Dio-Q-Phe-Z-Phe-Z-Phe-$R^2$ | Ic46 |
| $R^1$-Phe-Q-Cyc-Z-Dio-Z-Phe-$R^2$ | Ic47 |
| $R^1$-Phe-Q-Cyc-Z-Phe-Z-Dio-$R^2$ | Ic48 |
| $R^1$-Phe-Q-Cyc-Z-Dio-Z-Cyc-$R^2$ | Ic49 |
| $R^1$-Phe-Q-Cyc-Z-Cyc-Z-Dio-$R^2$ | Ic50 |
| $R^1$-Phe-Q-Cyc-Z-Dio-Z-Dio-$R^2$ | Ic51 |
| $R^1$-Phe-Q-Dio-Z-Dio-Z-Phe-$R^2$ | Ic52 |

| | |
|---|---|
| R¹-Phe-Q-Dio-Z-Phe-Z-Dio-R² | Ic53 |
| R¹-Phe-Q-Dio-Z-Dio-Z-Cyc-R² | Ic54 |
| R¹-Phe-Q-Dio-Z-Cyc-Z-Dio-R² | Ic55 |
| R¹-Phe-Q-Dio-Z-Dio-Z-Dio-R² | Ic56 |
| R¹-Phe-Q-Dio-Z-Phe-Z-Cyc-R² | Ic57 |
| R¹-Phe-Q-Dio-Z-Cyc-Z-Phe-R² | Ic58 |
| R¹-Phe-Q-Dio-Z-Cyc-Z-Cyc-R² | Ic59 |
| R¹-Phe-Q-Dio-Z-Phe-Z-Phe-R² | Ic60 |
| R¹-Phe-Q-Phe-Z-Dio-Z-Phe-R² | Ic61 |
| R¹-Phe-Q-Phe-Z-Phe-Z-Dio-R² | Ic62 |
| R¹-Phe-Q-Phe-Z-Dio-Z-Cyc-R² | Ic63 |
| R¹-Phe-Q-Phe-Z-Cyc-Z-Dio-R² | Ic64 |
| R¹-Phe-Q-Phe-Z-Dio-Z-Dio-R² | Ic65 |
| R¹-Dio-Z-Cyc-Q-Cyc-Z-Cyc-R² | Id1 |
| R¹-Dio-Z-Cyc-Q-Cyc-Z-Dio-R² | Id2 |
| R¹-Dio-Z-Cyc-Q-Cyc-Z-Phe-R² | Id3 |
| R¹-Dio-Z-Cyc-Q-Phe-Z-Cyc-R² | Id4 |
| R¹-Dio-Z-Cyc-Q-Phe-Z-Dio-R² | Id5 |
| R¹-Dio-Z-Cyc-Q-Phe-Z-Phe-R² | Id6 |
| R¹-Dio-Z-Cyc-Q-Dio-Z-Cyc-R² | Id7 |
| R¹-Dio-Z-Cyc-Q-Dio-Z-Phe-R² | Id9 |
| R¹-Dio-Z-Dio-Q-Cyc-Z-Cyc-R² | Id10 |
| R¹-Dio-Z-Dio-Q-Cyc-Z-Phe-R² | Id11 |
| R¹-Dio-Z-Dio-Q-Phe-Z-Cyc-R² | Id12 |
| R¹-Dio-Z-Dio-Q-Phe-Z-Dio-R² | Id13 |
| R¹-Dio-Z-Dio-Q-Phe-Z-Phe-R² | Id14 |
| R¹-Dio-Z-Dio-Q-Dio-Z-Cyc-R² | Id15 |
| R¹-Dio-Z-Dio-Q-Dio-Z-Phe-R² | Id16 |
| R¹-Dio-Z-Phe-Q-Cyc-Z-Cyc-R² | Id17 |
| R¹-Dio-Z-Phe-Q-Cyc-Z-Phe-R² | Id18 |
| R¹-Dio-Z-Phe-Q-Phe-Z-Cyc-R² | Id19 |
| R¹-Dio-Z-Phe-Q-Phe-Z-Dio-R² | Id20 |
| R¹-Dio-Z-Phe-Q-Phe-Z-Phe-R² | Id21 |
| R¹-Dio-Z-Phe-Q-Dio-Z-Cyc-R² | Id22 |
| R¹-Dio-Z-Phe-Q-Dio-Z-Phe-R² | Id23 |
| R¹-Cyc-Z-Cyc-Q-Dio-Z-Cyc-R² | Id24 |
| R¹-Cyc-Z-Cyc-Q-Dio-Z-Phe-R² | Id25 |
| R¹-Cyc-Z-Dio-Q-Cyc-Z-Cyc-R² | Id26 |
| R¹-Cyc-Z-Dio-Q-Cyc-Z-Phe-R² | Id27 |
| R¹-Cyc-Z-Dio-Q-Phe-Z-Cyc-R² | Id28 |
| R¹-Cyc-Z-Dio-Q-Phe-Z-Phe-R² | Id29 |
| R¹-Cyc-Z-Dio-Q-Dio-Z-Cyc-R² | Id30 |
| R¹-Cyc-Z-Dio-Q-Dio-Z-Phe-R² | Id31 |
| R¹-Cyc-Z-Phe-Q-Dio-Z-Cyc-R² | Id32 |
| R¹-Cyc-Z-Phe-Q-Dio-Z-Phe-R² | Id33 |
| R¹-Phe-Z-Cyc-Q-Dio-Z-Cyc-R² | Id34 |
| R¹-Phe-Z-Cyc-Q-Dio-Z-Phe-R² | Id35 |
| R¹-Phe-Z-Dio-Q-Cyc-Z-Cyc-R² | Id36 |
| R¹-Phe-Z-Dio-Q-Cyc-Z-Phe-R² | Id37 |
| R¹-Phe-Z-Dio-Q-Phe-Z-Cyc-R² | Id38 |
| R¹-Phe-Z-Dio-Q-Phe-Z-Phe-R² | Id39 |
| R¹-Phe-Z-Dio-Q-Dio-Z-Cyc-R² | Id40 |
| R¹-Phe-Z-Dio-Q-Dio-Z-Phe-R² | Id41 |
| R¹-Phe-Z-Phe-Q-Dio-Z-Cyc-R² | Id42 |
| R¹-Phe-Z-Phe-Q-Dio-Z-Phe-R² | Id43 | where the compounds of sub-formulae Ic1, Ic6, Ic12, Ic14, Ic26, Ic28, Ic49, Ic50, Ic54, Ic59, Ic63, Ic64, Id1, Id2, Id3, Id9, Id11, Id24, Id25, Id26, Id27 and Id30 are very particularly preferred.

Very particular preference is given to the following compounds:

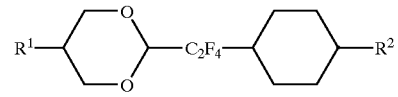

I1

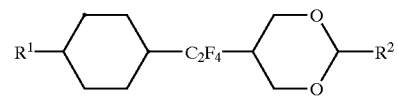

I2

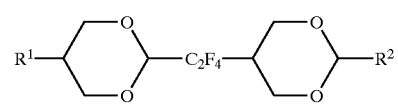

I3

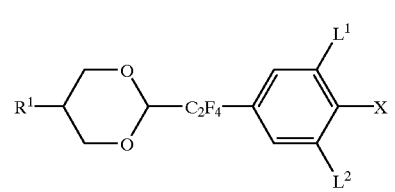

I4

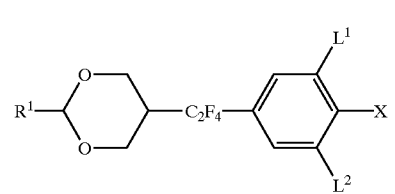

I5

-continued
I6
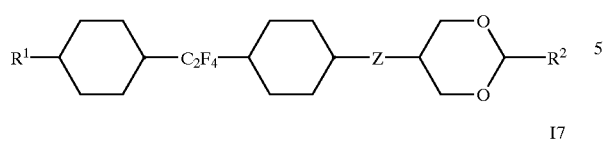
I7
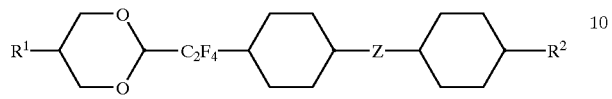
I8
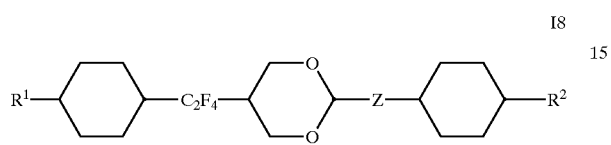
I9
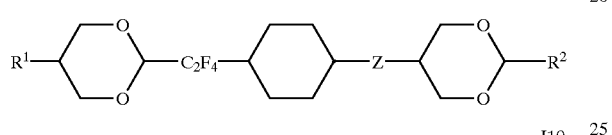
I10
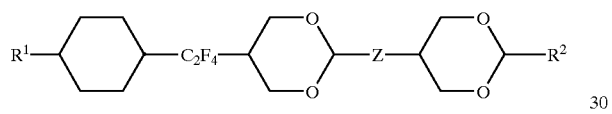
I11
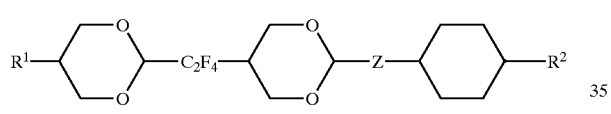
I12
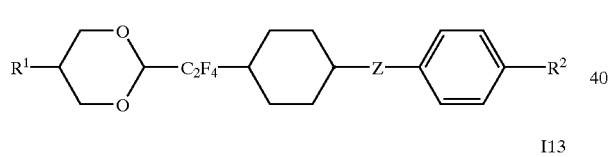
I13
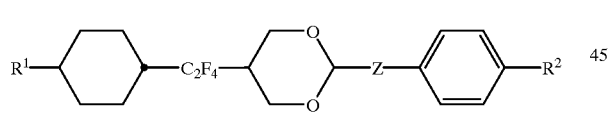
I14
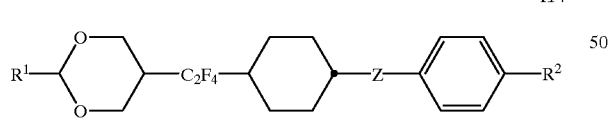
I15
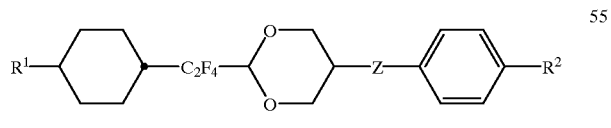
I16
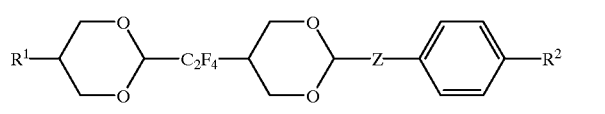
-continued
I17
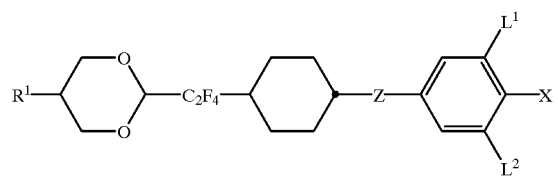
I18
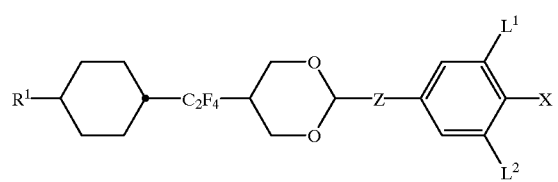
I19
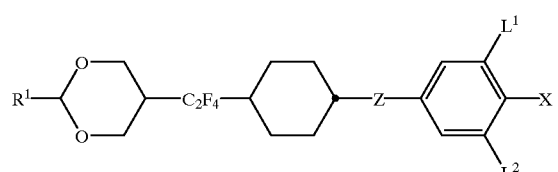
I20
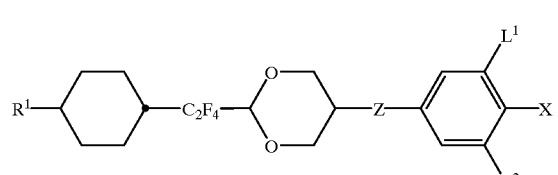
I21
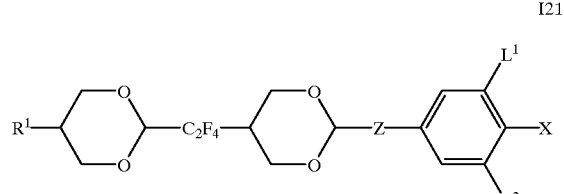
I22
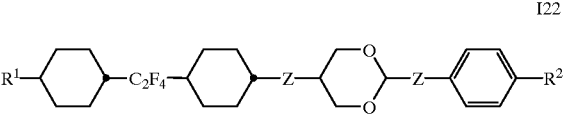
I23
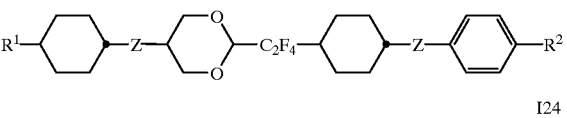
I24
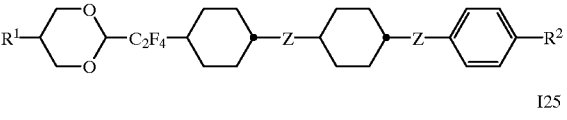
I25
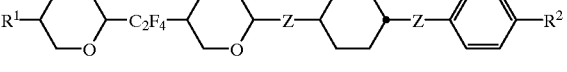

-continued

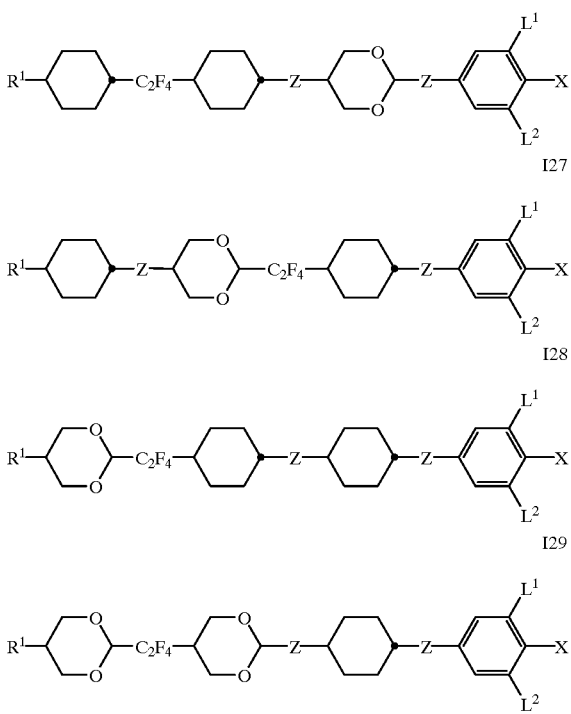

in which R¹, R² and Z are as defined above, X is F, Cl, CN or halogenated alkyl or alkoxy having 1 to 5 carbon atoms or halogenated alkenyl having 2 to 6 carbon atoms, and L¹ and L² are H or F. Particular preference is given to compounds of the formulae I4 and I8.

In the above preferred formulae, R¹ and R² are preferably alkyl or alkoxy having 1 to 12 carbon atoms or alkenyl or alkenyloxy having 2 to 7 carbon atoms.

Z is preferably —$CF_2CF_2$—, —$CH_2CH_2$— or a single bond, particularly preferably a single bond.

X is preferably F, Cl, CN, $CF_3$, $OCF_3$, $C_2F_5$, $OC_2F_5$, $C_3F_7$, $OC_3F_7$, $CHF_2$, $OCHF_2$, $CHFCF_3$, $CF_2CHF_2$, $C_2H_4CHF_2$, $CF_2CH_2CF_3$, $OCH_2CF_3$, $OCH_2CHF_2$, $OCF_2CHF_2$, $O(CH_2)_3CF_3$, $OCH_2C_2F_5$, $OCH_2CF_2CHF_2$, $OCH_2C_3F_7$, $OCHFCF_3$, $OCF_2CHFCF_3$, $OCH_2CF_2CHFCF_3$, $OCH=OF_2$, $OCF=OF_2$, $OCF=CFCF_3$, $OCF=CF—C_2F_5$, $CH=CHF$, $CH=CF_2$, $CF=CF_2$, $CF_2OCF_3$, in particular F, $CF_3$, $OCF_3$, $C_2F_5$, $OC_2F_5$, $C_3F_7$, $OC_3F_7$, $OCHFCF_3$, $OCHF_2$, $OCH=CF_2$, and $CF_2OCF_3$.

If R¹ and/or R² in the formulae above and below is an alkyl radical, this can be straight-chain or branched. It is preferably straight-chain, has 2, 3, 4, 5, 6 or 7 carbon atoms and accordingly is preferably ethyl, propyl, butyl, pentyl, hexyl or heptyl, furthermore methyl, octyl, nonyl, decyl, undecyl, dodecyl, tridecyl, tetradecyl or pentadecyl.

If R¹ and/or R² is an alkyl radical in which one $CH_2$ group has been replaced by —O—, this may be straight-chain or branched. It is preferably straight-chain and has 1 to 10 carbon atoms. The first $CH_2$ group of this alkyl radical has preferably been replaced by —O—, so that the radical R¹ attains the meaning of alkoxy and is preferably methoxy, ethoxy, propoxy, butoxy, pentyloxy, hexyloxy, heptyloxy, octyloxy or nonyloxy.

Furthermore, it is also possible for a $CH_2$ group elsewhere to be replaced by —O—, so that the radical R¹ and/or R² is preferably straight-chain 2-oxapropyl methoxymethyl), 2-(= ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R¹ and/or R² is an alkyl radical in which one $CH_2$ group has been replaced by —CH=CH—, this may be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl.

Examples of particularly preferred alkenyl groups are vinyl, 1E-propenyl, 1E-butenyl, 1E-pentenyl, 1E-hexenyl, 1E-heptenyl, 3E-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

If R¹ and/or R² is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R¹ is an alkyl radical in which one $CH_2$ group has been replaced by unsubstituted or substituted —CH=CH— and an adjacent $CH_2$ group has been replaced by CO or CO—O or O—CO—, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

If R¹ is an alkyl or alkenyl radical which is monosubstituted by CN or $CF_3$, this radical is preferably straight-chain, and the substitution by CN or $CF_3$ is in the ω-position.

If R¹ and/or R² is an alkyl or alkenyl radical which is at least monosubstituted by halogen, this radical is preferably straight-chain, and halogen is preferably F or Cl. In the case of polysubstitution, halogen is preferably F. The resulting radicals also include perfluorinated radicals. In the case of monosubstitution, the fluorine or chlorine substituent can be in any desired position, but is preferably in the ω-position.

Compounds of the formula I containing branched wing groups R¹ and/or R² may occasionally be of importance owing to better solubility in the customary liquid-crystalline base materials, but in particular as chiral dopants if they are optically active. Smectic compounds of this type are suitable as components for ferroelectric materials.

Branched groups of this type generally contain not more than one chain branch. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and the sub-formulae, preference is given to those in which at least one of the radicals present therein has one of the preferred meanings indicated.

In the compounds of the formula I, preference is given to the stereoisomers in which the rings Cyc and piperidine are 1,4-disubstituted. Those of the above-mentioned formulae which contain one or more groups Pyd, Pyr and/or Dio in each case cover the two 2,5-positional isomers.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions. Use can be made here of variants which are known per se, but are not mentioned here in greater detail.

The compounds of the formula I can be prepared, for example, as shown in the following reaction schemes or analogously thereto. Further synthetic methods are indicated in the examples.

Scheme 1

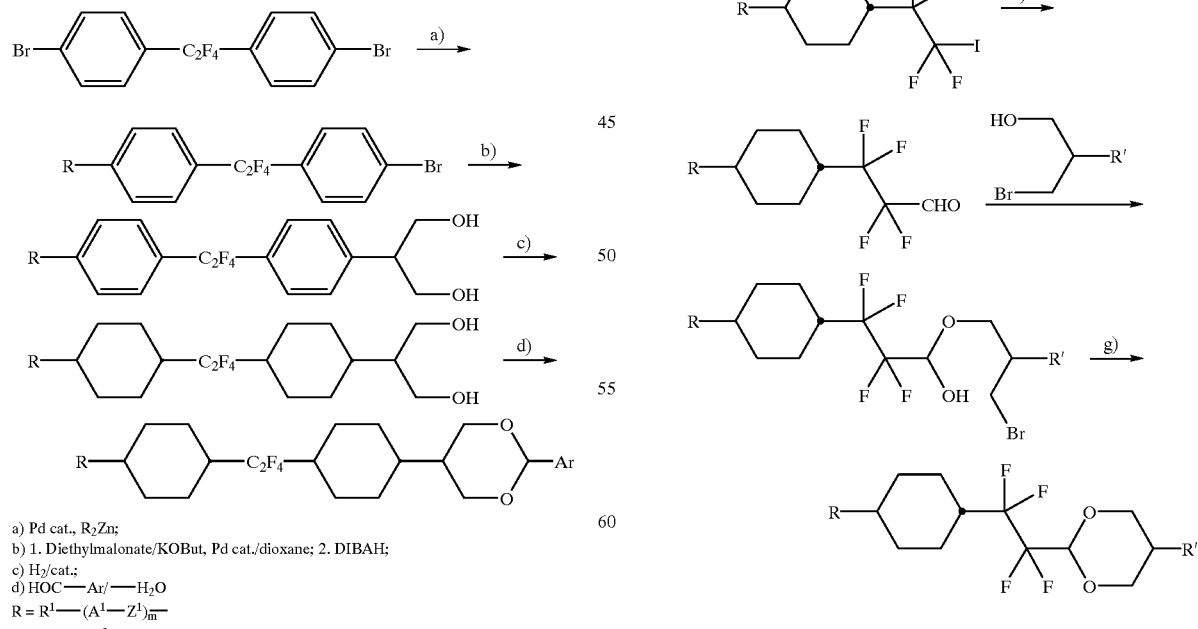

a) Pd cat., $R_2Zn$;
b) 1. Diethylmalonate/KOBut, Pd cat./dioxane; 2. DIBAH;
c) $H_2$/cat.;
d) HOC—Ar/—$H_2O$
$R = R^1$—$(A^1$—$Z^1)_{\overline{m}}$
Ar = Phe—$R^2$ Scheme 2

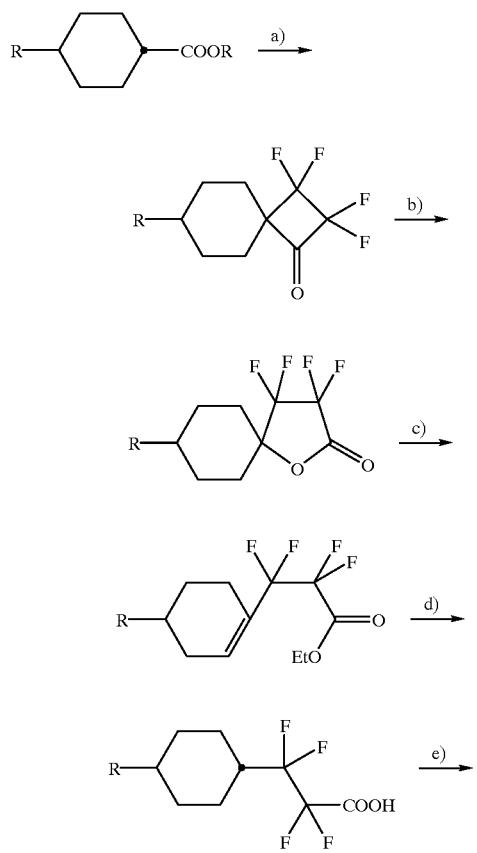

-continued a) 1. LDA, 2. CF$_2$═CF$_2$;
b) MCPBA/CH$_2$Cl$_2$;
c) EtOH, H$_2$SO$_4$;
d) 1. H$_2$/cat., 2. KOH;
e) 1. Ag$_2$O, 2. I$_2$;
f) DMF, Zn(Cu), AIBN;
g) NaH
R = R$^1$—(A$^1$—Z$^1$)$_{\overline{m}}$—
R' = —(Z$^2$—A$^4$)$_n$—R$^2$ Scheme 3

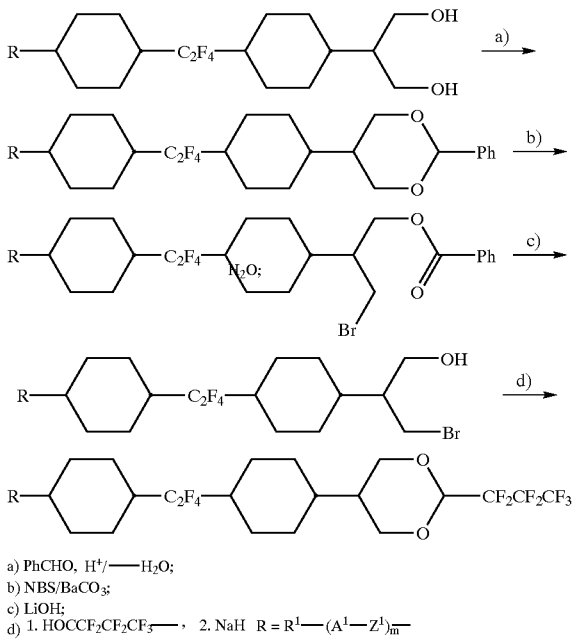

a) PhCHO, H$^+$/——H$_2$O;
b) NBS/BaCO$_3$;
c) LiOH;
d) 1. HOCCF$_2$CF$_2$CF$_3$——, 2. NaH   R = R$^1$—(A$^1$—Z$^1$)$_{\overline{m}}$—

Scheme 4

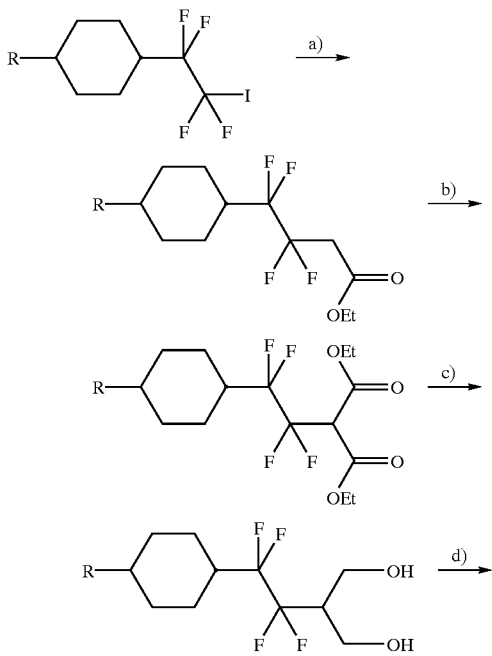

-continued

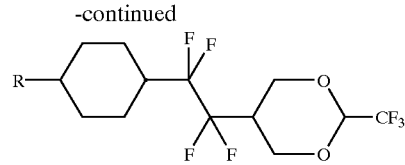

a) 1. Na$_2$S$_2$O$_4$/NaHCO$_3$, MeCN/H$_2$O, 2. Jones oxidation,
   3. EtOH/ H$^+$/——H$_2$O;
b) 1. LDA, 2. ClCOOEt;
c) LiAlH$_4$;
d) analogously to a) –d) from Scheme 3
R = R$^1$—(A$^1$—Z$^1$)$_{\overline{m}}$—

The starting materials can, if desired, also be formed in situ by not isolating them from the reaction mixture, but instead immediately converting them further into the compounds of the formula I.

Esters of the formula I can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

Suitable reactive derivatives of the said carboxylic acids are in particular the acid halides, especially the chlorides and bromides, furthermore the anhydrides, azides or esters, in particular alkyl esters having 1–4 carbon atoms in the alkyl group.

Suitable reactive derivatives of the said alcohols and phenols are in particular the corresponding metal alkoxides and phenoxides respectively, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Water-immiscible solvents can at the same time advantageously be used for removal by azeotropic distillation of the water formed during the esterification. It may occasionally also be possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between −50° C. and +250° C., preferably between −20° C. and +80° C. At these temperatures, the esterification reactions are generally complete after from 15 minutes to 48 hours.

In detail, the reaction conditions for the esterification depend substantially on the nature of the starting materials used. Thus, the reaction of a free carboxylic acid with a free alcohol or phenol is generally carried out in the presence of a strong acid, for example a mineral acid, such as hydrochloric acid or sulfuric acid. A preferred reaction procedure is to react an acid anhydride or, in particular, an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline-earth metal hydroxides, such as calcium hydroxide, or organic bases, such as triethylamine, pyridine, lutidine, collidine or quinoline. A further preferred embodiment of the esterification comprises first converting the alcohol or phenol into the sodium or potassium alkoxide or phenoxide, for example by treatment with ethanolic sodium hydroxide or potassium hydroxide solution, and isolating the product and reacting it with an acid anhydride or, in particular, acid chloride.

Nitriles can be obtained by replacement of halogens using copper cyanide or alkali metal cyanide.

In a further process for the preparation of compounds of the formula I in which $Z^1$ or $Z^2$ is —CH=CH—, an aryl halide is reacted with an olefin in the presence of a tertiary amine and in the presence of a palladium catalyst (R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, is also suitable as solvent. Examples of suitable palladium catalysts are its salts, in particular Pd(II) acetate, with organophosphorus(III) compounds, such as, for example, triarylphosphines. This process can be carried out in the presence or absence of an inert solvent at temperatures between about 0C and 150° C., preferably between 20° C. and 100° C.; suitable solvents are, for example, nitrites, such as acetonitrile, or hydrocarbons, such as benzene or toluene. The aryl halides and olefins employed as starting materials are frequently commercially available and can be prepared by processes known from the literature, for example by halogenation of corresponding parent compounds or by elimination reactions on corresponding alcohols or halides.

In this way, it is possible to prepare, for example, stilbene derivatives. The stilbenes may furthermore be prepared by reacting a 4-substituted benzaldehyde with the corresponding phosphorus ylide by the Wittig method. However, it is also possible to prepare tolans of the formula I by using monosubstituted acetylene instead of the olefin (Synthesis 627 (1980) or Tetrahedron Lett. 27, 1171 (1986)).

For the coupling of aromatic compounds, it is furthermore possible to react aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$ or $Z^2$ is —C≡C— can also be prepared via the Fritsch-Buttenberg-Wiechell rearrangement (Ann. 279, 319, 1984), in which 1,1-diaryl-2-haloethylenes are rearranged to give diarylacetylenes in the presence of strong bases.

Tolans of the formula I can also be prepared by brominating the corresponding stilbenes and subsequently subjecting the product to dehydrohalogenation. Use can be made here of variants of this reaction which are known per se, but are not mentioned here in greater detail.

Ethers of the formula I are obtainable by etherification of corresponding hydroxyl compounds, preferably corresponding phenols, the hydroxyl compound advantageously first being converted into a corresponding metal derivative, for example into the corresponding alkali metal alkoxide or alkali metal phenoxide, by treatment with NaH, NaNH$_2$, NaOH, KOH, Na$_2$CO$_3$ or K$_2$CO$_3$. This metal derivative can then be reacted with the appropriate alkyl halide, alkyl sulfonate or dialkyl sulfate, advantageously in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° C. and 100° C.

In order to prepare the laterally substituted fluorine or chlorine compounds of the formula I, corresponding aniline derivatives can be reacted with sodium nitrite and either with tetrafluoroboric acid (in order to introduce an F atom) or with copper(I) chloride (in order to introduce a chlorine atom), to give the diazonium salts, which are then decomposed thermally at temperatures of 100–140° C.

The linking of an aromatic ring to a non-aromatic ring or of two non-aromatic rings is preferably obtained by condensation of an organolithium or organomagnesium compound with a ketone if an aliphatic group $Z^1$ is to be between the rings.

The organometallic compounds are prepared, for example, by metal-halogen exchange (for example in accordance with Org. React. 6, 339–366 (1951)) between the corresponding halogen compound and an organolithium compound, such as, preferably, tert-butyllithium or lithium naphthalenide, or by reaction with magnesium turnings.

The linking of two aromatic rings to an aromatic ring is preferably carried out by Friedel-Crafts alkylation or acylation by reacting the corresponding aromatic compounds with Lewis acid catalysis. Suitable Lewis acids are, for example, SnCl$_4$, ZnCl$_2$, AlCl$_3$ and TiCl$_4$.

Furthermore, the linking of two aromatic rings can be carried out by the Ullmann reaction (for example Synthesis 1974, 9) between aryl iodides with copper iodide, but preferably between an aryl copper compound and an aryl iodide, or by the Gomberg-Bachmann reaction between an aryldiazonium salt and the corresponding aromatic compound (for example Org. React. 2, 224 (1944)).

The tolans of the formula I ($Z^1$=—C≡C—) are prepared, for example, by reaction of the corresponding aryl halides with an acetylide in a basic solvent with transition-metal catalysis; palladium catalysts can preferably be used here, in particular a mixture of bis(triphenylphosphine) palladium(II) chloride and copper iodide in piperidine as solvent.

In addition, the compounds of the formula I can be prepared by reducing a compound which contains one or more reducible groups and/or C—C bonds in place of H atoms, but otherwise conforms to the formula I.

Suitable reducible groups are preferably carbonyl groups, in particular keto groups, furthermore, for example, free or esterified hydroxyl groups or aromatically bonded halogen atoms. Preferred starting materials for the reduction are compounds which conform to the formula I, but contain a —CH=CH— group in place of a —CH$_2$CH$_2$— group and/or contain a —CO— group in place of a —CH$_2$— group and/or contain a free or functionally derived (for example in the form of its p-toluenesulfonate) OH group in place of an H atom.

The reduction can be carried out, for example, by catalytic hydrogenation at temperatures between about 0° C. and about 200° C. and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which may be employed in the form of oxides (for example $PtO_2$ or PdO), on a support (for example Pd on carbon, calcium carbonate or strontium carbonate) or in finely divided form.

Ketones can also be reduced by the methods of Clemmensen (using zinc, zinc amalgam or tin and hydrochloric acid, advantageously in aqueous-alcoholic solution or in the heterogeneous phase with water/toluene at temperatures between about 80 and 120° C.) or Wolff-Kishner (using hydrazine, advantageously in the presence of alkali, such as KOH or NaOH, in a high-boiling solvent, such as diethylene glycol or triethylene glycol, at temperatures between about 100 and 200° C.) to give the corresponding compounds of the formula I which contain alkyl groups and/or —$CH_2CH_2$— bridges.

Furthermore, reductions using complex hydrides are possible. For example, arylsulfonyloxy groups can be removed reductively using $LiAlH_4$, in particular p-toluenesulfonyloxymethyl groups can be reduced to methyl groups, advantageously in an inert solvent, such as diethyl ether or THF, at temperatures between about 0 and 100° C. Double bonds can be hydrogenated using $NaBH_4$ or tributyltin hydride in methanol.

The starting materials are either known or can be prepared analogously to known compounds.

The liquid-crystalline media according to the invention preferably comprise from 2 to 40 components, in particular from 4 to 30 components, as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

  1

  2

  3

  4

  5

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

$R^1$ and/or $R^{11}$ are each, independently of one another, alkyl, alkenyl, alkoxy, alkoxyalkyl, alkenyloxy or alkanoyloxy having up to 8 carbon atoms, —F, —Cl, —CN, —NCS, —(O)$_i$—CH$_{3-(K+L)}$F$_K$Cl$_L$, where i is 0 or 1 and K and L are 1, 2 or 3.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are denoted by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is called group B, R" is —F, —Cl, —NCS or —(O)$_i$CH$_{3-(k+l)}$F$_k$Cl$_l$, where i is 0 or 1, and k and l are 1, 2 or 3; the compounds in which R" has this meaning are denoted by the sub-formulae 1b, 2b, 3b, 4b and 5b. Particular preference is given to those compounds of the sub-formulae 1b, 2b, 3b, 4b and 5b in which R" is —F, —Cl, —NCS, —$CF_3$, —$OCHF_2$ or —$OCF_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is called group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a-5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably:

Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5%–90% and in particular from 10% to 90%.

The media according to the invention preferably comprise from 1 to 40%, particularly preferably from 5 to 30%, of the compounds according to the invention. Further preferred media are those which comprise more than 40%, in particular from 45 to 90%, of compounds according to the invention. The media preferably comprise three, four or five compounds according to the invention.

The liquid-crystal mixtures which can be used in accordance with the invention are prepared in a manner conventional per se. In general, the desired amount of the components used in a lesser amount is dissolved in the components making up the principal constituent, expediently at elevated temperature. It is also possible to mix solutions of the components in an organic solvent, for example in acetone, chloroform or methanol, and to remove the solvent again after thorough mixing, for example by distillation. It is also possible to prepare the mixtures in another conventional manner, for example by using premixes, for example homologue mixtures, or using so-called "multi-bottle" systems.

The dielectrics may also comprise further additives known to the person skilled in the art and described in the literature. For example, 0–15%, preferably 0–10%, of pleochroic dyes and/or chiral dopants can be added. The additives are each employed in concentrations of from 0.01 to 6%, preferably from 0.1 to 3%. However, the concentration data for the other constituents of the liquid-crystal mixtures, i.e. of the liquid-crystalline or mesogenic compounds, are given without taking into account the concentration of these additives.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. n and m are integers, preferably 1, 2, 3, 4, 5, 6, 7, 8, 9, 10, 11 and 12, where n=m or n≠m. The coding in Table B is self-evident.

In Table A, only the acronym for the parent structure is given, followed, separated from the acronym for the parent structure by a hyphen, by a code for the substituents $R^{1*}$, $R^{2*}$, $L^{1*}$ and $L^{2*}$:

| Code for $R^1$, $R^2$<br>$R^2$, $L^1$, $L^2$, $L^3$ | $R^2$ | $L^1$ | $L^2$ | $L^3$ |
|---|---|---|---|---|
| nm | $C_nH_{2n+1}$ | $C_mH_{2m+1}$ | H | H | H |
| nOm | $OC_nH_{2n+1}$ | $C_mH_{2m+1}$ | H | H | H |
| nO.m | $C_nH_{2n+1}$ | $OC_mH_{2m+1}$ | H | H | H |
| n | $C_nH_{2n+1}$ | CN | H | H | H |
| nN.F | $C_nH_{2n+1}$ | CN | H | H | F |
| nN.F.F | $C_nH_{2n+1}$ | CN | H | F | F |
| nF | $C_nH_{2n+1}$ | F | H | H | H |
| nOF | $OC_nH_{2n+1}$ | F | H | H | H |
| nF.F | $C_nH_{2n+1}$ | F | H | H | F |
| nmF | $C_nH_{2n+1}$ | $C_mH_{2m+1}$ | F | H | H |
| nOCF3 | $C_nH_{2n+1}$ | $OCF_3$ | H | H | H |
| n-Vm | $C_nH_{2n+1}$ | —CH=CH—$C_mH_{2m+1}$ | H | H | H |
| nV-Vm | $C_nH_{2n+1}$—CH=CH— | —CH=CH—$C_mH_{2m+1}$ | H | H | H |

Preferred mixture components are shown in Tables A and B:

TABLE A

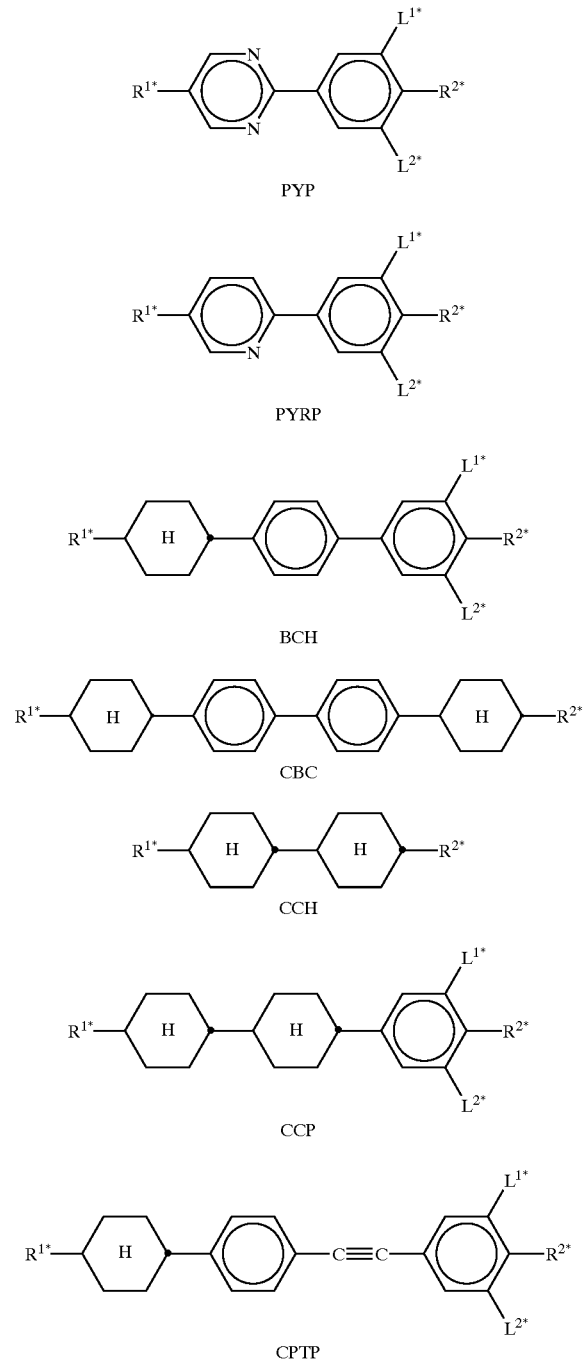

PYP

PYRP

BCH

CBC

CCH

CCP

CPTP

TABLE A-continued
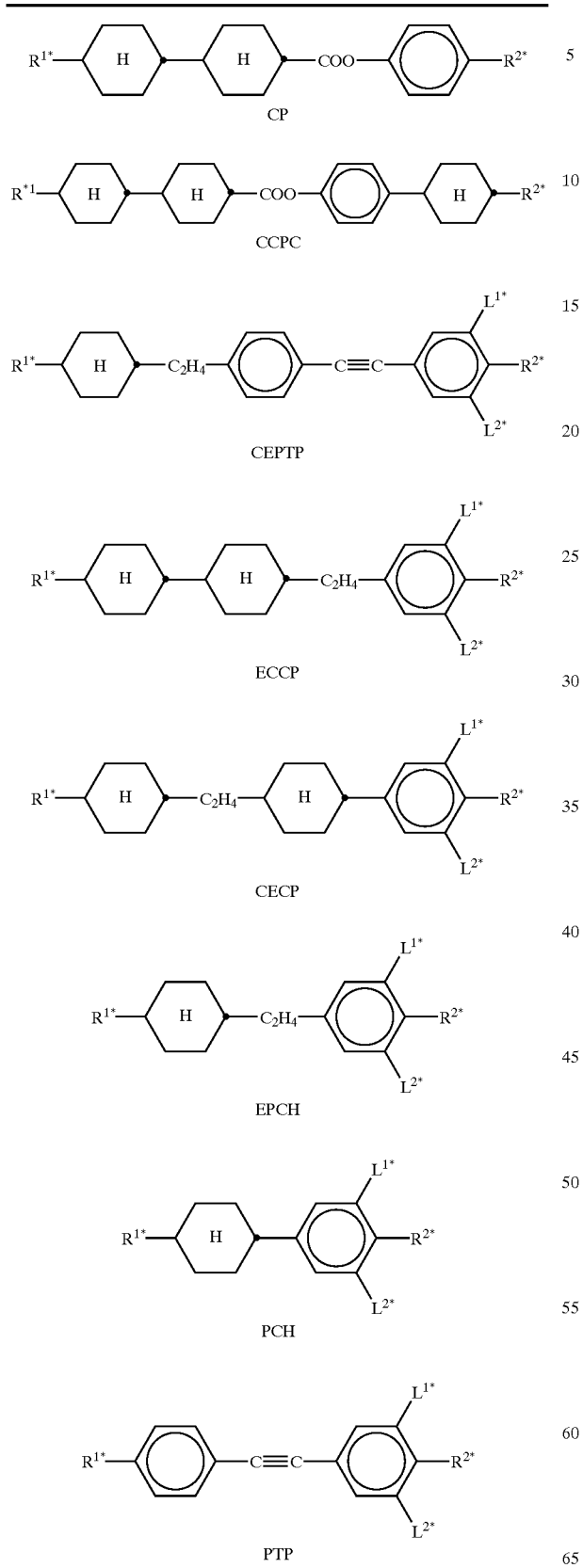
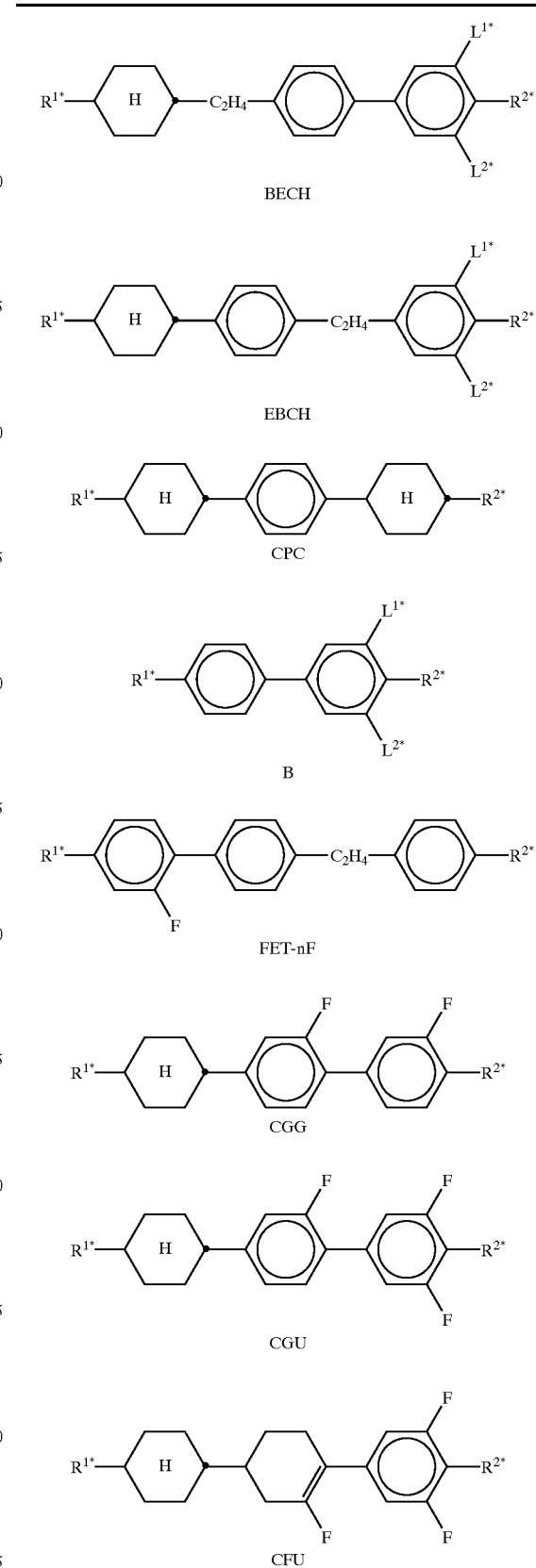

TABLE B
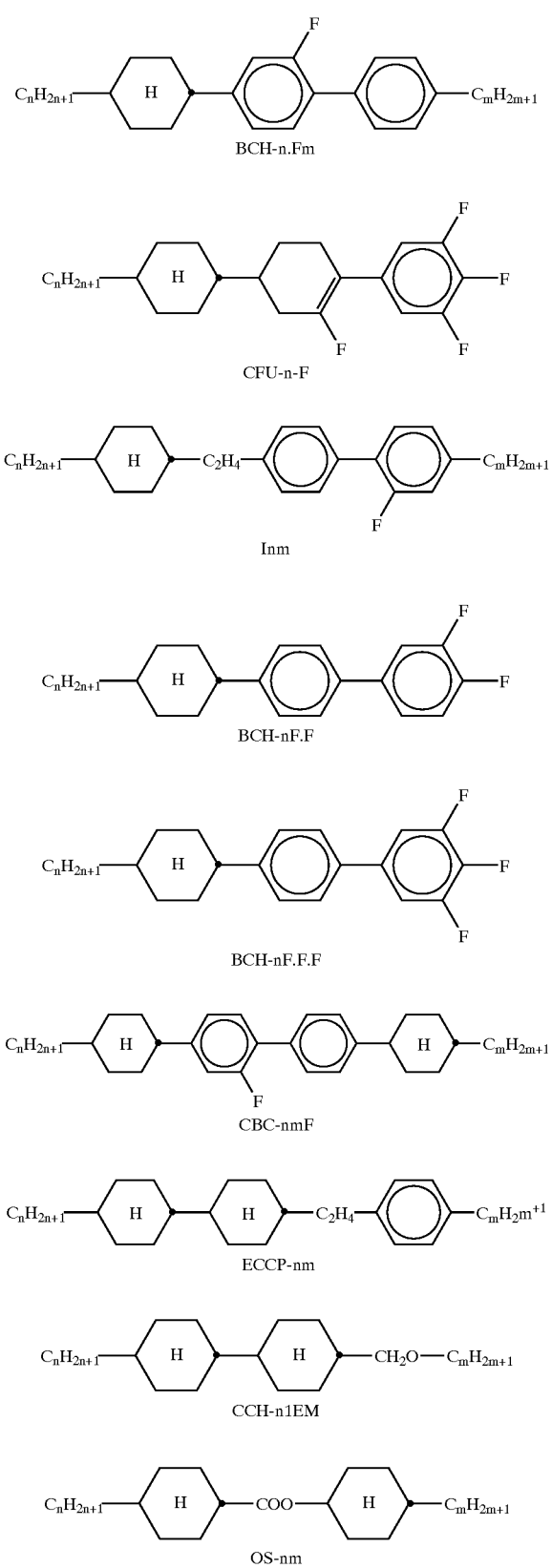
TABLE B-continued
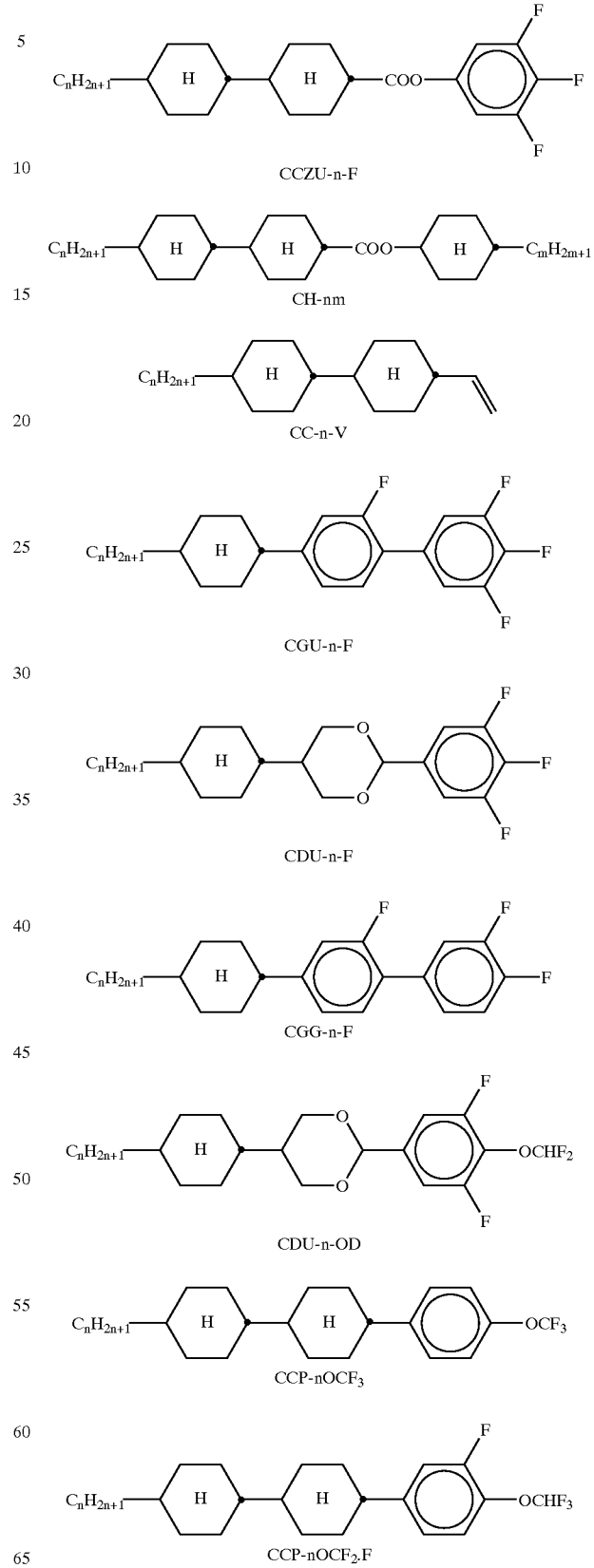

TABLE B-continued

CCP-nF.F.F

CCP-nOCF₃.F

CCQU-n-F

CQCU-n-F

Dec-U-n-F

GPTU-n-F

CZGU-n-F

CC-1V-V1

CC-n-V1

CCTU-n-F

CECG-n-OT

CECU-n-OT

CCQPC-n-m

TABLE C

Table C indicates dopants which are usually employed in the liquid-crystalline mixtures.

C 15

CB 15

CM 21

TABLE C-continued

Table C indicates dopants which are usually employed in the liquid-crystalline mixtures.

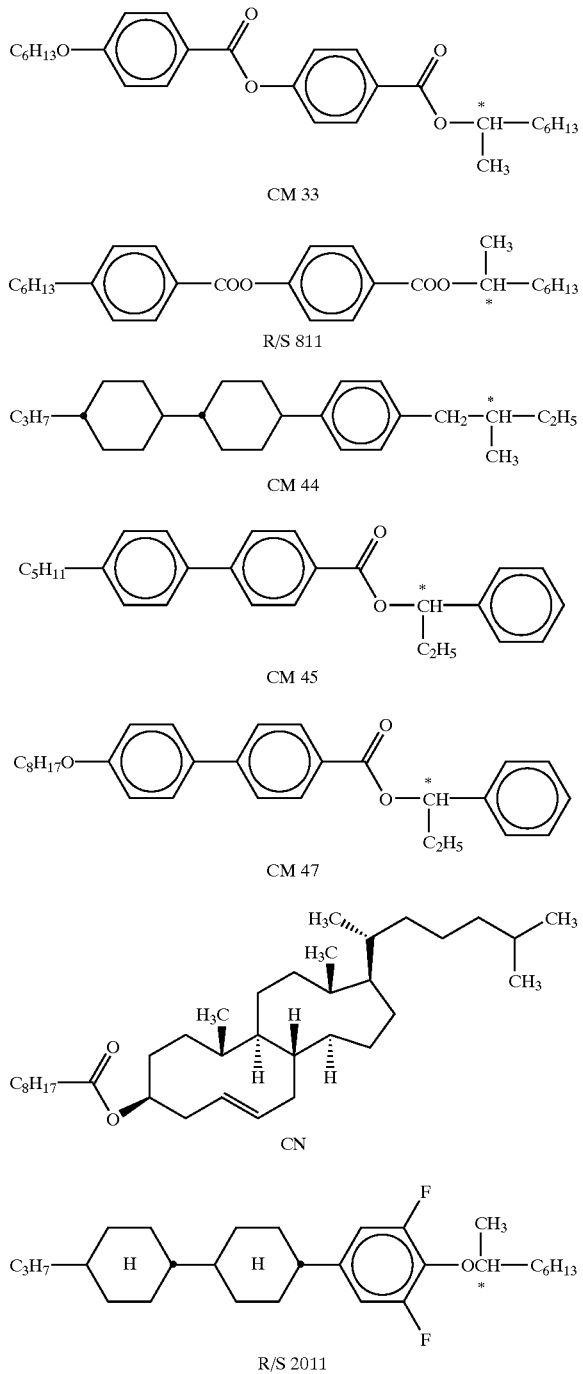

EXAMPLES

The examples below are intended to illustrate the invention without representing a limitation. Above and below, percentages are percent by weight. All temperatures are given in degrees Celsius. m.p. denotes melting point, cl.p. clearing point. Furthermore, C=crystalline state, N=nematic phase, S=smectic phase and I=isotropic phase. The numbers between these symbols represent the transition temperatures. Δn denotes the optical anisotropy (589 nm, 20° C.), and Δε the dielectric anisotropy (1 kHz, 20° C.).

Δn and Δε values of the compounds according to the invention were obtained by extrapolation from liquid-crystalline mixtures consisting of 10% of the respective compounds according to the invention and 90% of the commercially available liquid crystal ZLI 4792 (Merck, Darmstadt).

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

Above and below, the following abbreviations are used:
DCC dicyclohexylcarbodiimide
DIBAH diisobutylaluminium hydride
DMF dimethylformamide
DMPU 1,3-dimethyl-3,4,5,7 G-tetrahydro-2(1H)-pyrimidinone
LDA lithium diisopropylamide
MCPBA 3-chloroperoxybenzoic acid
NBS N-bromosuccinimide
n-BuLi n-butyllithium
RT room temperature (about 20° C.)
THF tetrahydrofuran

Example 1

The compound of the following formula

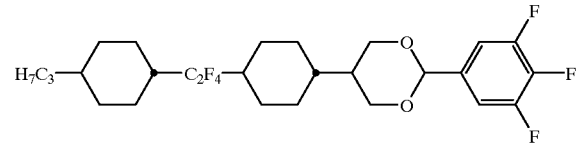

is prepared as follows in accordance with reaction scheme 1:

1.1 mol of magnesium turnings are suspended in 50 ml of THF and reacted with a solution of 1.0 mol of 1-bromopropane in 500 ml of THF to give the Grignard reagent. The mixture is cooled to 10° C., and 0.5 mol of zinc bromide dissolved in 2000 ml of THF are added dropwise. 10 mol percent of bis (diphenylphosphino) ferrocenylpalladium dichloride are added to the organozinc compound, 0.5 mol of dibromodiphenyl-1,1,2,2-tetrafluoroethane in THF is added dropwise, the mixture is stirred overnight at RT and subjected to conventional work-up.

0.6 mol of diethyl malonate, 0.6 mol of potassium tert-butoxide, 0.06 mol of palladium acetate, 0.06 mol of tri-t-butylphosphine and 0.4 mol of p-propylphenyl(p-bromophenyl)-1,1,2,2-tetrafluoroethane are dissolved in 500 ml of 1,4-dioxane, the mixture is refluxed overnight and subjected to conventional work-up.

The resultant malonate is added with ice cooling at RT to a solution of 1.2 mol of diisobutylaluminium hydride in 500 ml of THF and subjected to conventional work-up. The resultant propanediol dissolved in THF is fully hydrogenated using Rh/C at 50 bar of $H_2$ and RT, worked up and crystallized.

Particular preference is given to mixtures according to the invention which, besides one or more compounds of the formula I, comprise two, three or more compounds selected from Table B.

The entire disclosure of all applications, patents and publications, cited above, and of corresponding German application No. 10039378.0, filed Aug. 11, 2000 is hereby incorporated by reference.

0.1 mol of the pure 1-(4-propylcyclohexyl)-2-(4-(1,3-dihydroxy-2-propyl)cyclohexyl)-1,1,2,2-tetrafluoroethane are boiled on a water separator with 0.1 mol of 3,4,5-trifluorobenzaldehyde and 10 mol percent of p-toluenesulfonic acid in 400 ml of toluene and, after cooling, subjected to conventional work-up.

$\Delta\epsilon = 13.2$; $\Delta n = 0.072$

The following compounds according to the invention are obtained analogously using the corresponding precursors:

Examples 2–18

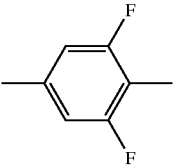

| | $R^1$ | $A^4$ | $R^2$ |
|---|---|---|---|
| (2) | n-Ethyl | 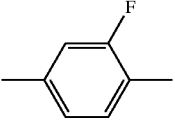 | F |
| (3) | n-Butyl | 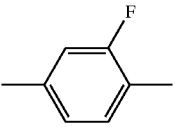 | F |
| (4) | n-Pentyl | 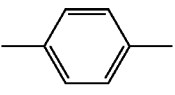 | F |
| (5) | n-Propyl | 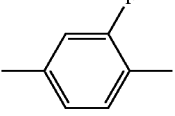 | F |
| (6) | n-Pentyl | 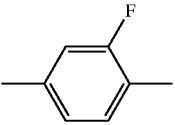 | F |
| (7) | n-Propyl | 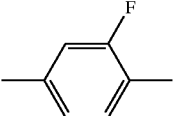 | CN |

-continued

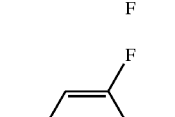

| | $R^1$ | $A^4$ | $R^2$ |
|---|---|---|---|
| (8) | n-Pentyl | 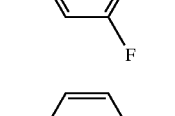 | CN |
| (9) | n-Propyl | 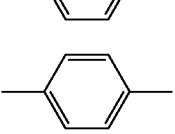 | CN |
| (10) | n-Pentyl | 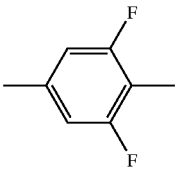 | CN |
| (11) | n-Propyl | 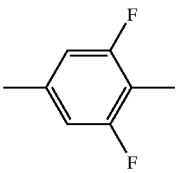 | CN |
| (12) | n-Propyl | 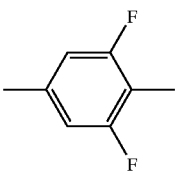 | Cl |
| (13) | n-Pentyl | 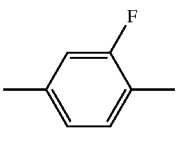 | Cl |
| (14) | n-Propyl | 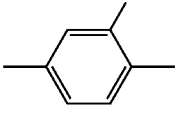 | $OCF_3$ |
| (15) | n-Pentyl | 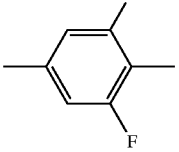 | $OCF_3$ |
| (16) | n-Propyl | | $OCF_3$ |
| (17) | n-Pentyl | | $OCF_3$ |

-continued

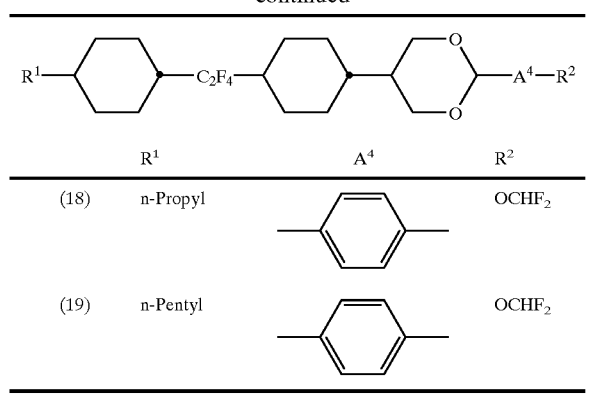

| | R¹ | A⁴ | R² |
|---|---|---|---|
| (18) | n-Propyl | (phenyl) | OCHF₂ |
| (19) | n-Pentyl | (phenyl) | OCHF₂ |

Example 20

The compound of the following formula

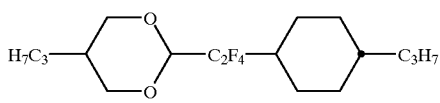

is prepared as follows in accordance with reaction scheme 2:

0.17 mol of n-BuLi in hexane are added dropwise at −60° C. to 0.17 mol of diisopropylamine dissolved in 150 ml of THF. The mixture is stirred at −60° C. for 1 hour, 0.17 mol of DMPU and 0.17 mol of methyl trans-4-(trans-4-propylcyclohexyl)cyclohexanecarboxylate dissolved in 250 ml of THF are added dropwise to the reaction mixture, and the mixture is again stirred at −60° C. for 1 hour. 0.17 mol of tetrafluoroethene are subsequently passed into the reaction mixture at from −35° C. to −45° C. The mixture is subjected to conventional work-up. The resultant spirocyclobutanone is reacted with 1.1 equivalents of MCPBA in dichloromethane at RT, worked up and dissolved in crude form in 500 ml of ethanol. 10 ml of concentrated sulfuric acid are added, and the mixture is refluxed for 5 hours. After work-up, the resultant ester is chromatographed on silica gel (toluene:ethyl acetate 1:1).

0.1 mol of ethyl 3-(4-propylcyclohexenyl)-2,2,3,3-tetrafluoropropionate are dissolved in THF and hydrogenated using Pd/C at atmospheric pressure and RT. After the solvent has been removed, the residue is taken up in methanol, 0.1 mol of powdered potassium hydroxide is added, the mixture is stirred at RT for 2 hours and, after cooling, subjected to conventional work-up.

0.5 equivalent of silver(I) oxide in water is added to the resultant propionic acid. The mixture is stirred at RT for 1 hour, and 0.5 equivalent of finely powdered iodine is added at RT. Finally, the mixture is heated at 40° C. for a further hour and then subjected to conventional work-up. The resultant iodide is taken up in 200 ml of DMF, and 1.0 equivalent of zinc activated by copper sulfate in water is added. 1.0 mol percent of AIBN is added, and the mixture is warmed at 100° C. for 2 hours. After cooling, the mixture is subjected to conventional work-up.

0.05 mol of 3-(4-propylcyclohexyl)-2,2,3,3-tetrafluoropropionaldehyde and 0.05 mol of 2-n-propyl-3-hydroxypropyl bromide are stirred for 1 hour at RT in 70 ml of THF. 0.06 mol of sodium hydride are subsequently added, and the mixture is heated at 40° C. for 45 minutes. The mixture is subjected to conventional work-up and crystallized from hexane.

$\Delta\epsilon=0.6$; $\Delta n=0.040$

The following compounds according to the invention are obtained analogously using the corresponding precursors:

Examples 21–29

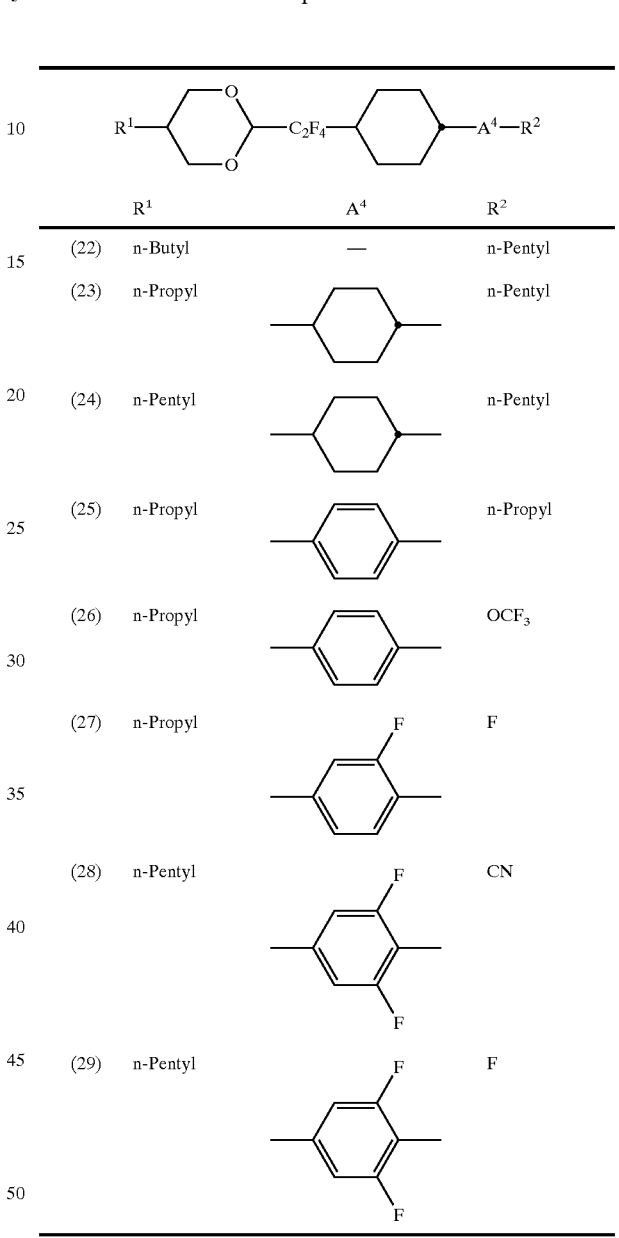

| | R¹ | A⁴ | R² |
|---|---|---|---|
| (22) | n-Butyl | — | n-Pentyl |
| (23) | n-Propyl | (cyclohexyl) | n-Pentyl |
| (24) | n-Pentyl | (cyclohexyl) | n-Pentyl |
| (25) | n-Propyl | (phenyl) | n-Propyl |
| (26) | n-Propyl | (phenyl) | OCF₃ |
| (27) | n-Propyl | (2,3-difluorophenyl) | F |
| (28) | n-Pentyl | (2,3,5-trifluorophenyl) | CN |
| (29) | n-Pentyl | (2,3,5-trifluorophenyl) | F |

Example 30

The compound of the following formula

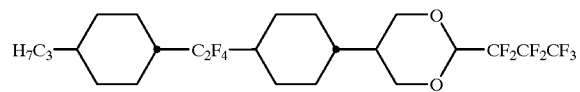

is prepared in accordance with reaction scheme 3 (R=n-propyl).

$\Delta\epsilon=8.9$; $\Delta n=0.037$

The following compounds according to the invention are obtained analogously using the corresponding precursors:

Examples 31–39

| | R¹ | A¹ | R² |
|---|---|---|---|
| (31) | n-Propyl | — | CF₃ |
| (32) | n-Propyl | — | C₂F₅ |
| (33) | n-Pentyl | cyclohexyl | C₂F₅ |
| (34) | n-Pentyl | cyclohexyl | C₃F₇ |
| (35) | n-Propyl | phenyl | C₃F₇ |
| (36) | n-Pentyl | phenyl | C₃F₇ |
| (37) | n-Pentyl | 2-F-phenyl | C₃F₇ |
| (38) | n-Pentyl | 2,3,5-triF-phenyl | C₂F₅ |
| (39) | n-Pentyl | 2,3,5-triF-phenyl | C₃F₇ |

Example 40

The compound of the following formula

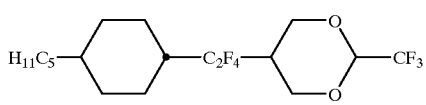

is prepared in accordance with the above scheme 4 (R=n-pentyl).

Δε=11.5; Δn=0.034

The following compounds according to the invention are obtained analogously using the corresponding precursors:

Examples 41–49

| | R¹ | A¹ | R² |
|---|---|---|---|
| (41) | n-Propyl Δε = 12.1, Δn = 0.033 | — | CF₃ |
| (42) | n-Butyl | — | CF₃ |
| (43) | n-Propyl | — | C₂F₅ |
| (44) | n-Propyl | cyclohexyl | CF₃ |
| (45) | n-Pentyl | cyclohexyl | CF₃ |
| (46) | n-Propyl | phenyl | CF₃ |
| (47) | n-Pentyl | phenyl | C₂F₅ |
| (48) | n-Pentyl | 2-F-phenyl | CF₃ |
| (49) | n-Propyl | 2,3,5-triF-phenyl | CF₃ |

Example 50

A liquid-crystal mixture comprising

| | |
|---|---|
| CCP-2F.F.F | 10% |
| CCP-3F.F.F | 10% |
| CCP-20CF3 | 6% |
| CCP-30CF3 | 9% |
| CGU-3-F | 11% |
| CGU-5-F | 10% |
| BCH-3F.F.F | 5% |
| CCZU-2-F | 7% |
| CCZU-3-F | 15% |
| CCZU-5-F | 7% |
| Example (40) | 6% |
| Example (41) | 4% | has the following properties:

| Clearing point: | 70.1°C. |
|---|---|
| Δε: | 10.7 |
| Δn: | 0.0807 |
| Rotational viscosity: | 154 |

Comparative Example

A liquid-crystal mixture comprising

| CCP-2F.F.F | 10% |
|---|---|
| CCP-3F.F.F | 10% |
| CCP-3OCF3 | 6% |
| CGU-2-F | 11% |
| CGU-3-F | 11% |
| CGU-5-F | 10% |
| BCH-3F.F.F | 5% |
| CCZU-2-F | 7% |
| CCZU-3-F | 15% |
| CCZU-5-F | 7% |
| ECCP-5F.F | 8% |

| Clearing point: | 68.9°C. |
|---|---|
| Δε: | 10.7 |
| Δn: | 0.0868 |
| Rotational viscosity: | 147 | has a lower clearing point and higher birefringence compared with the mixture from Example (50).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula I

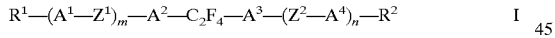     I in which $R^1$ and $R^2$, independently of one another, are H, —CN, —F, Cl, —OCN, —NCS, —$NO_2$, or an alkyl radical having 1–12 carbon atoms which is unsubstituted or monosubstituted or polysubstituted by halogen, CN or $CF_3$, and in which one or more $CH_2$ groups are each, independently of one another, optionally replaced by —O—, —S—, —CO—, —CO—O—, —O—CO—, —O—CO—O—, —CH=CH—, —CH=CF—, —CF=CF—, —C≡C— or

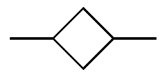

in such a way that S and/or O atoms are not linked directly to one another, $A^1$, $A^2$, $A^3$ and $A^4$, independently of one another, are a) trans-1,4-cyclohexylene, in which one or more non-adjacent $CH_2$ groups are optionally replaced by —O— and/or —S—, b) 1,4-phenylene, in which, one or two CH groups are optionally replaced by N, c) a radical selected from the group consisting of 1,4-bicyclo [2.2.2]octylene, piperidine-1,4-diyl, naphthalene-2,6-diyl, decahydronaphthalene-2,6-diyl and 1,2,3,4-tetrahydro-naphthalene-2,6-diyl, or d) 1,4-cyclohexenylene, in which the radicals a), b) and d) are optionally substituted by CN or halogen, and where at least one of the radicals $A^1$, $A^2$, $A^3$ and $A^4$ is 1,3-dioxane-2,5-diyl, $Z^1$ and $Z^2$ are each, independently of one another, —O—, —$CH_2$O—, —$OCH_2$—, —CO—O—, —O—CO—, —$CF_2$O—, —$OCF_2$—, —$CF_2CF_2$—, —$CH_2CH_2$—, —CH=CH—, —CH=CF—, —CF=CF—, —C≡C— or a single bond, and m and n, independently of one another, are 0, 1 or 2, where m+n is 0, 1 or 2.

2. A compound of the formula I according to claim 1, wherein $A^1$, $A^2$, $A^3$ and $A^4$ are selected from the group consisting of 1,3-dioxane-2,5-diyl, trans-cyclohexane-1,4-diyl or unsubstituted or substituted 1,4-phenylene.

3. A compound of the formula I according to claim 1, wherein $R^1$ and $R^2$ are alkyl or alkoxy having 1 to 12 carbon atoms or alkenyl or alkenyloxy having 2 to 10 carbon atoms.

4. A compound of the formula I according to claim 1 wherein n is 1 or 2, $A^4$ is 1,4-phenylene which is monosubstituted or disubstituted by F or CN, and $R^2$ is F, Cl, CN or halogenated alkyl or alkoxy having 1 to 5 carbon atoms or halogenated alkenyl having 2 to 6 carbon atoms.

5. A compound of the formula I according to claim 1, wherein $Z^1$ and $Z^2$ are each independently —$CH_2CH_2$—, —$CF_2CF_2$— or a single bond.

6. A compound of the formula I of claim 1 wherein only one or two of $A^1$, $A^2$, $A^3$ and $A^4$ is 1,3-dioxane-2,5-diyl.

7. A compound of the formula I of claim 1 wherein the compound contains a trans-1,4-cyclohexylene radical.

8. A compound of the formula I of claim 1, which is a compound of one of formulae Ia, Ib, Ic or Id:

bicyclic compounds of the sub-formula Ia

     Ia tricyclic compounds of the sub-formula Ib

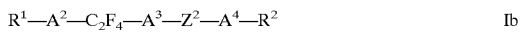     Ib tetracyclic compounds of the sub-formulae Ic or Id

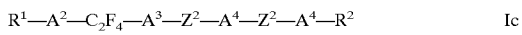     Ic

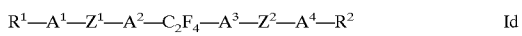     Id

9. A compound of the formula I of claim 1, which is a compound of one of formulae I1 to I29:

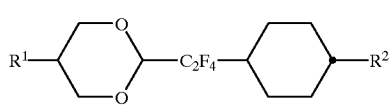     I1

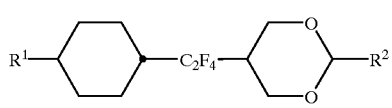     I2

-continued
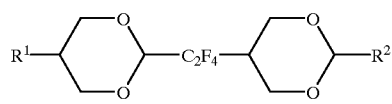
I3
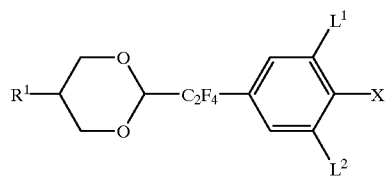
I4
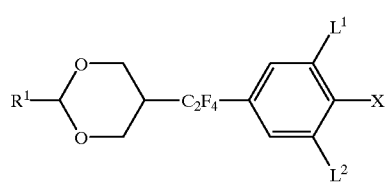
I5
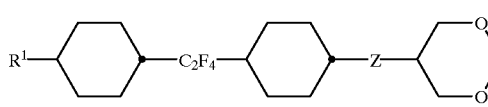
I6
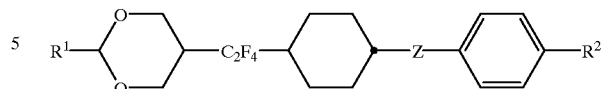
I7
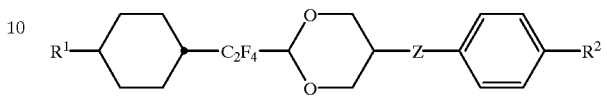
I8
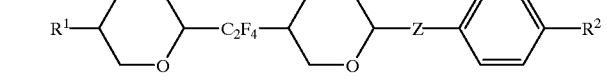
I9
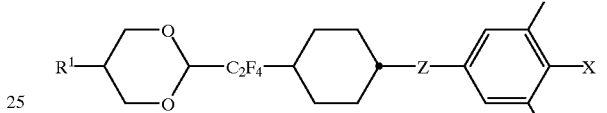
I10
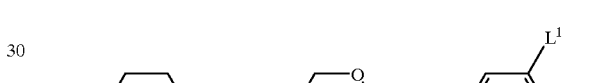
I11
I12
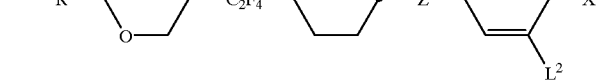
I13
-continued
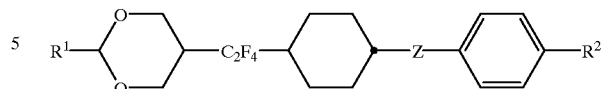
I14
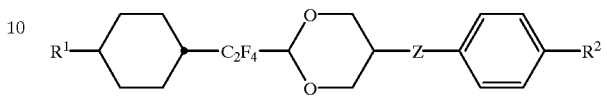
I15
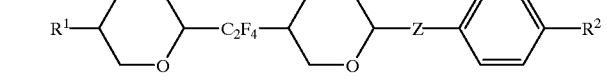
I16
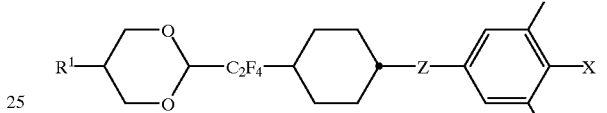
I17
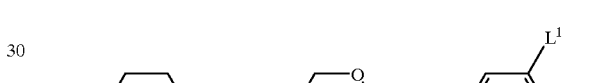
I18
I19
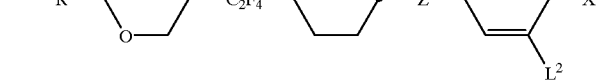
I20
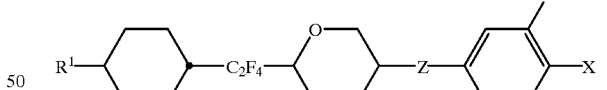
I21
I22

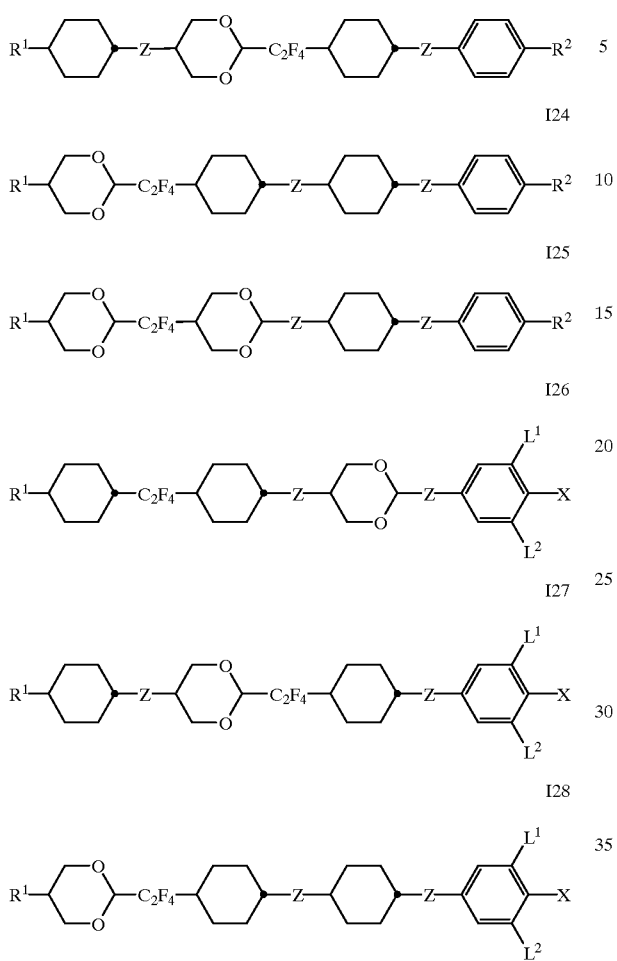

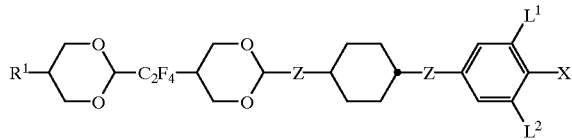

in which $R^1$, and $R^2$ are as defined above, Z is as defined above for $Z^1$ and $Z^2$, X is F, Cl, CN or halogenated alkyl or alkoxy having 1 to 5 carbon atoms or halogenated alkenyl having 2 to 6 carbon atoms, and $L^1$ and $L^2$ are H or F.

10. A liquid-crystalline medium having at least two liquid-crystalline components, which comprises at least one compound of the formula I according to claim 1.

11. A liquid-crystal display element, which comprises a liquid-crystalline medium according to claim 10.

12. A reflective or transflective liquid-crystal display element, which comprises, as dielectric, a liquid-crystalline medium according to claim 10.

13. An electro-optical display element, which comprises, as dielectric, a liquid-crystalline medium according to claim 10.

14. A TN, STN, IPS or TFT liquid crystal display comprising a liquid-crystal display element of claim 11.

15. A compound of claim 1, which exhibits a clearing point of $\geq 65°$ C.

16. A liquid-crystalline medium of claim 10, wherein compounds of the formula I make up from 1 to 40% by weight of the medium.

17. A liquid-crystalline medium of claim 10, wherein compounds of the formula I make up from 5 to 30% by weight of the medium.

18. A liquid-crystalline medium of claim 10, wherein compounds of the formula I make up from 45 to 90% by weight of the medium.

19. A liquid-crystalline medium of claim 10, wherein the medium contains three, four or five different compounds of the formula I.

* * * * *